(12) United States Patent
Olver et al.

(10) Patent No.: US 7,968,756 B2
(45) Date of Patent: Jun. 28, 2011

(54) PROCESS AND APPARATUS FOR PRODUCTION OF VINYL CHLORIDE MONOMER

(75) Inventors: John W. Olver, Blacksburg, VA (US); Jason Andrew Simmons, Blacksburg, VA (US)

(73) Assignee: Wessex Incorporated, Blacksburg, VA (US)

( * ) Notice: Subject to any disclaimer, the term of this patent is extended or adjusted under 35 U.S.C. 154(b) by 323 days.

(21) Appl. No.: 12/190,227

(22) Filed: Aug. 12, 2008

(65) Prior Publication Data

US 2010/0041927 A1   Feb. 18, 2010

(51) Int. Cl.
C07C 17/25   (2006.01)
(52) U.S. Cl. ....................................................... 570/226
(58) Field of Classification Search .................... 570/226
See application file for complete search history.

(56) References Cited

U.S. PATENT DOCUMENTS

| | | | |
|---|---|---|---|
| 4,746,759 A * | 5/1988 | Dummer et al. | 570/226 |
| 5,873,951 A | 2/1999 | Wynns et al. | |
| 6,139,649 A | 10/2000 | Wynns | |
| 6,228,253 B1 | 5/2001 | Gandman | |
| 6,312,652 B1 | 11/2001 | Duncan | |
| 6,337,459 B1 | 1/2002 | Terwijn et al. | |
| 6,368,494 B1 | 4/2002 | Tong | |
| 6,454,995 B1 | 9/2002 | Tong | |
| 6,497,809 B1 | 12/2002 | Brown et al. | |
| 6,537,388 B1 | 3/2003 | Wynns et al. | |
| 6,830,676 B2 | 12/2004 | Deevi | |
| 7,105,047 B2 * | 9/2006 | Simmons et al. | 106/600 |
| 7,132,577 B2 | 11/2006 | Jo et al. | |
| 2005/0058851 A1 | 3/2005 | Smith et al. | |
| 2006/0127700 A1 | 6/2006 | Jo et al. | |

FOREIGN PATENT DOCUMENTS

WO   WO2007/064288   6/2007

* cited by examiner

*Primary Examiner* — Jafar Parsa
(74) *Attorney, Agent, or Firm* — Johnston Holroyd; Mary-Jacq Holroyd

(57) ABSTRACT

Process and apparatus to form vinyl chloride monomer from ethylene dichloride in a cracking furnace, including a firebox chamber having a thermal protective layer disposed on refractory walls and/or process tubes disposed within the chamber, a quencher to form vinyl chloride monomer, and fractionator separate products. The thermal protective layer which contains an inorganic adhesive for metal/alloy tubes or colloidal silica and/or colloidal alumina for refractory walls or ceramic tubes, a filler, and one or more emissivity agents.

17 Claims, 3 Drawing Sheets

PROCESS AND APPARATUS FOR PRODUCTION OF VINYL CHLORIDE MONOMER

BACKGROUND OF INVENTION

In the production of vinyl chloride monomer, pyrolysis furnaces, also known as cracking furnaces, are used to crack ethylene dichloride (EDC) in the presence of catalysts in the process to form vinyl chloride monomer (VCM), known as chloroethene in IUPAC nomenclature, to ultimately produce polyvinyl chloride (PVC). Cracking the EDC in a continuous feed production process is the predominant process for making VCM. In the production process, chlorine is reacted with ethylene to produce EDC, which is further cracked to form VCM and the byproduct hydrochloric acid. Oxygen may optionally be added to the process resulting in the additional byproduct of water. The hydrochloric acid may further be fed back into the process as a source of chlorine. PVC is then produced by polymerizing the VCM, removing excess VCM, and drying the product. The VCM is polymerized in a batch reactor to produce PVC. Excess VCM is then removed and the PVC is dried. The dried PVC may be packaged and stored to be delivered for further manufacturing processes.

Almost all VCM produced is used to manufacture PVC resins. The PVC is used in a large variety of end products including consumer products, packaging, and construction. Vaporized EDC is dried and passed over a catalyst packed in stainless steel tubes that are directly heated in a cracking furnace. The hot effluent gases are quenched and the condensed gases fed into a fractionating tower operating under pressure. The product VCM is formed by condensing the overhead vapors in a water condenser. The VCM is then filtered and sent to either a storage tank for further processing to produce PVC or sold to other manufacturers that make PVC.

Each cracking furnace has a refractory lined firebox containing a multiplicity of high alloy metal or ceramic cracking lines, composed of process pipes, through the interior passages of which flows the EDC feedstock to be cracked. Various catalysts may be added to the EDC feedstock including oxygen, recycled hydrogen chloride, and other well known catalysts. Refractories used to line the firebox are classified as basic, high aluminum, silica, fireclay and insulating. Special refractories include silicon carbide graphite, zircon, zirconia, and fused cast, among others. Refractory lining may be formed of bricks, castables, or thermal ceramic fiber to cover the interior of the firebox. A suitable amount of diluting steam may be included in the process. Burners are located on the floor and/or walls of the firebox to provide the heat necessary. The heat transfers through the metallic/ceramic materials of the reaction lines into the hydrocarbon feedstock that flows within the reaction lines. Known metallic cracking lines may be as long as 2000 feet and may be coiled in a serpentine shape that runs vertically up and down in the firebox or it may be as short as 40 feet in a straight single pass through the firebox.

The process tubes are heated using convection heating or a combination of convection and radiant heat. The tube may be made of a metal alloy or ceramic. Alloys include most stainless steel, cast alloys, wrought alloys, carbon steel and the like, which are well known to those skilled in the art. The refractory materials, both hard and ceramic fiber, incorporated into the firebox contain the heat permitting the process tubes to be heated for the cracking or related reactions to occur. The fireboxes themselves can deliver an increased radiant heat load to the process tubes.

Traditional process tubes are fabricated from cast or wrought, high alloy stainless steels. Coke layers form along the inner surfaces of the process tubes during normal operation resulting in reduced mass flow through the tube and a reduction in heat transfer through the sides of the tubes. Additional formation of metal carbides along the tube walls, referred to as carburization, further reduces the structural life of the furnace tubes. The furnace must be periodically shut down in order to remove the deposits of coke. This factor results in a substantial loss of production and facility downtime. Furthermore, coke is an excellent thermal insulator requiring higher temperatures resulting in higher fuel costs and shorter tube life.

Process tubes resistant to coking and carburization are desirable. Efforts to produce such resistant process tubes have concentrated on developing a variety of new alloys that are resistant to carburization and reduce the development of coke layers. Some of these efforts have concentrated on layering different alloys on the tubes. Research has shown that, like aluminides, aluminum and silicon containing alloys, iron, chrome, and certain other alloys also prevent coking and carburization. Ceramic and alloys containing silicon have also been found potentially useful.

The use of a coating film to inhibit coke formation in an ethylene dichloride to a vinyl chloride monomer pyrolysis cracker is known. U.S. Pat. No. 7,132,577 and U.S. Patent Application Publication No. 2006/127,700 by Jo et al., published on Nov. 7, 2006 and Jun. 15, 2006 respectively, disclose a coating film for inhibiting coke formation in an ethylene dichloride pyrolysis cracker and a method of producing the coating film. Specifically, the invention of Jo et al. teaches inhibiting coke formation by coating a boron compound on a heat-transfer surface of the cracker, resulting in a 50% or greater reduction in coke formation. The coating film appears to have been applied solely to the internal surface of the process tubes. Specifically, the inner surface of the process tubes are coated with the boron compound composition. The ethylene chloride conversion and the selectivity to a vinyl chloride monomer during the pyrolysis reaction are not affected by the reduction in coke formation.

Similarly, U.S. Pat. Nos. 6,368,494 and 6,454,995 issued to Tong, on Apr. 9, 2002 and Sep. 24, 2002 respectively, teaches a method for reducing coke in an EDC-VCM furnaces by exposing the heat transfer surfaces to a phosphite compound. The phosphite compound either alone or in combination with a carrier is applied to the inner surface of the process tubes by feeding the phosphite compounds through the tubes either prior to or contemporaneous with the EDC feedstock. The phosphite compounds are fed through the process tubes, which are exposed to the stream for thirty minutes to two days.

U.S. Pat. No. 6,228,253 issued to Gandman on May 8, 2001 discloses a method for removing and suppressing coke formation during pyrolysis by cutting off the feedstock to one or more coils (process tubes) and adding a decoking additive to the steam flow comprised of a group IA/IIA metal salt, which coats the coils inner surface with a "glass layer" that inhibits coke formation.

U.S. Pat. No. 6,830,676 issued on Dec. 14, 2004 and assigned to Chrysalis Technologies Incorporated teaches coking and carburization resistant iron aluminides for hydrocarbon cracking. In this invention, the cracking tubes have a lining of iron aluminide alloy which is fouling and corrosion resistant. U.S. Patent Application No. 2005/058,851 discloses a composite tube for an ethylene pyrolysis furnace and methods of manufacture and joining same wherein the tube comprises an outer shell made from a wrought or cast heat resistant alloy and an inner core made from another alloy whose composition approximates a powder form. Both outer shell and inner core may be extruded to form the process tubes.

U.S. Pat. No. 5,873,951, assigned to Alon, Inc., issued on Feb. 23, 1999 shows a diffusion coated ethylene furnace process tube in which the inner surface of the process tubes are diffusion coated with a sufficient amount of chromium or chromium and silicon to form a first coating having a thickness of at least two mils which is then cleaned, neutralized and grit blasted. A second coating of aluminum or aluminum and silicon is then diffused onto the first coating to form a total coating thickness of at least five mils; the second coating is also cleaned and polished to provide a smooth uniform surface. Reportedly, less coking occurs in these coated tubes.

U.S. Pat. No. 6,139,649, also assigned to Alon, Inc., issued on Oct. 31, 2000, teaches a diffusion method for coating high temperature nickel chromium alloy products which produces ethylene furnace process tubes having a high temperature nickel chromium alloy product coated on the inner surface thereof. The inner coating has a first layer of chromium or chromium and silicon covered by a second layer of aluminum, magnesium, silicon and manganese which in turn is covered by a third layer of rare earth metals such as yttrium and zirconium. After each layer is applied the tube is heat treated, and finally after the final layer has been applied the final surface is treated with argon and nitrogen to stabilize the surface oxides, and can be polished to minimize sites for carbon buildup. Less coking occurs in these coated process tubes.

U.S. Pat. No. 6,537,388 issued on Mar. 25, 2003 and also assigned to Alon, Inc. discloses a surface alloy system conversion for high temperature applications in which chromium, silicon, aluminum, and optionally manganese are diffused onto the surface of a high temperature ally product, to provide a coating having improved resistance to carburization and catalytic coke formation.

U.S. Pat. No. 6,337,459 issued on Jan. 8, 2002 and assigned to Daido Tokushuko Kabushiki Kaisha teaches a multi-layered anti-coking heat resisting metal tube and a method of manufacturing the process tube in which a preferably powdered alloy is applied to the inner and/or outer surface of the process tube.

PCT application International Publication No. WO2007/064288 published on Jun. 7, 2007, and applied for by Sandvik Intellectual Property AB discloses a metallic tube for heating a medium or subject outside or inside thereof by heat transfer thorough the walls of the tube in which a layer of essential $Al_2O_3$ is formed on the surfaces thereof when heated to at least 750° C. At least one of the external and the internal surface of the tube is coated by one of a metal, metal alloy and metal compound, which after oxidation forms as a layer having an emissivity coefficient exceeding 0.7 or by a layer essentially consisting of a metal oxide which has an emissivity coefficient exceeding 0.7.

Although, the majority of reaction cracking lines are comprised of metallic tubes, alternative compositions of the reaction cracking lines are possible. For example, U.S. Pat. No. 6,312,652 issued on Nov. 6, 2001 and assigned to Stone & Webster Engineering Corp. discloses a ceramic drip pipe and tube reactor for ethylene production. The reaction lines of the furnace are fabricated of a ceramic refractory feed inlet pipe coaxially located with a ceramic refractory tube to define an annular space therebetween which is, in part, located without and within the radiant heating firebox volume of such furnace, this to provide for a zone wherein hot cracked olefin product gas is quenched in temperature in such annular space outside of the firebox and a cracking zone within the firebox within which hydrocarbon feed is cracked to an olefin containing product gas composition. The ceramic refractory material construction of the '652 patent permits such a pipe-tube reaction line structure to be exposed to a much greater heat/temperature content of which the firebox is capable than reaction lines of conventional metallic construction. Cracking predominantly occurs within the annular space, meaning that the cylindrical ceramic refractory structures may be of diameters sufficient to provide for high strength structures. Greater firebox temperatures allow the use of a shorter reaction line structure.

U.S. Pat. No. 6,497,809 issued on Dec. 24, 2002 and assigned to Phillips Petroleum Company discloses a method for prolonging the effectiveness of a pyrolytic cracking tube treated for the inhibition of coke formation during cracking in which the tubes have tin and silicon deposited on the surface exposed to the hydrocarbon feed functioning as an antifoulant for inhibiting the formation of coke to desulfurize a sulfur-containing feedstock.

SUMMARY OF THE INVENTION

The present invention, drawn to pyrolysis furnace constructions and process used in the production of vinyl chloride monomers, each furnace construction includes a firebox defining a chamber having a thermal protective layer disposed on at least part of the refractory walls and/or on at least one process tube disposed within the firebox chamber. The thermal protective layer consisting of a high emissivity multifunctional coating. The thermal protective layer is disposed on the exposed surfaces within the firebox, including the external surfaces of the process tubes, and within the process tubes. The refractory walls are covered with refractory material, including bricks, castables or thermal ceramic fiber, as is well known in the art, and are composed of silica, fireclay, high alumina, and the like and combinations thereof, as is also known in the art.

Vaporized EDC is dried and passed over a catalyst packed in the process tubes that are directly heated in a cracking furnace. The hot effluent gases are quenched and the condensed gases fed into a fractionating tower operating under pressure. The product VCM is formed by condensing the overhead vapors in a water condenser. The VCM is then filtered and sent to either a storage tank for further processing to produce PVC or sold to other manufacturers that make PVC.

The thermal protective layer on the metal/alloy surfaces of process tubes may contain from about 5% to about 30% of an inorganic adhesive, from about 45% to about 92% of a filler, and from about 2% to about 20% of one or more emissivity agents, in a dry admixture. An alternative thermal protective layer which may be disposed on ceramic surfaces of either refractory wall or process tubes may contain from about 5% to about 35% of colloidal silica, from about 23% to about 79% of a filler, and from about 2% to about 20% of one or more emissivity agents. Either thermal protective layer of the present invention may further contain from about 1% to about 5% of a stabilizer.

An aspect of the present invention is that the thermal protective layer limits coking; therefore, less maintenance is required, resulting in less downtime, and increasing the amount of continuous production runs possible.

Another aspect of the present invention is that it generates uniform heating of the refractory walls and process tubes, Uniform heating of the refractory walls results in improved cracking ratios, less maintenance, energy savings and increased production.

Yet another aspect of the present invention is a dramatic increase in cost efficiently and production. Overall, the cost efficiency and production yields are increased permitting a greater profit and less waste.

A further aspect of the present invention is that it reduces the outside skin temperature of the furnace.

Yet a further aspect of the present invention is the increased heat transfer from the furnace refractory walls to the process tubes and the increased thermal flux across the tubes, and improves the cracking rate/ratio.

These and other aspects of the present invention will become readily apparent upon further review of the following drawings and specification.

BRIEF DESCRIPTION OF THE DRAWINGS

The novel features of the described embodiments are specifically set forth in the appended claims; however, embodiments relating to the structure and process of making the present invention, may best be understood with reference to the following description and accompanying drawings.

Similar reference characters denote corresponding features consistently throughout the attached drawings.

DETAILED DESCRIPTION OF PREFERRED EMBODIMENTS

Figure 1:
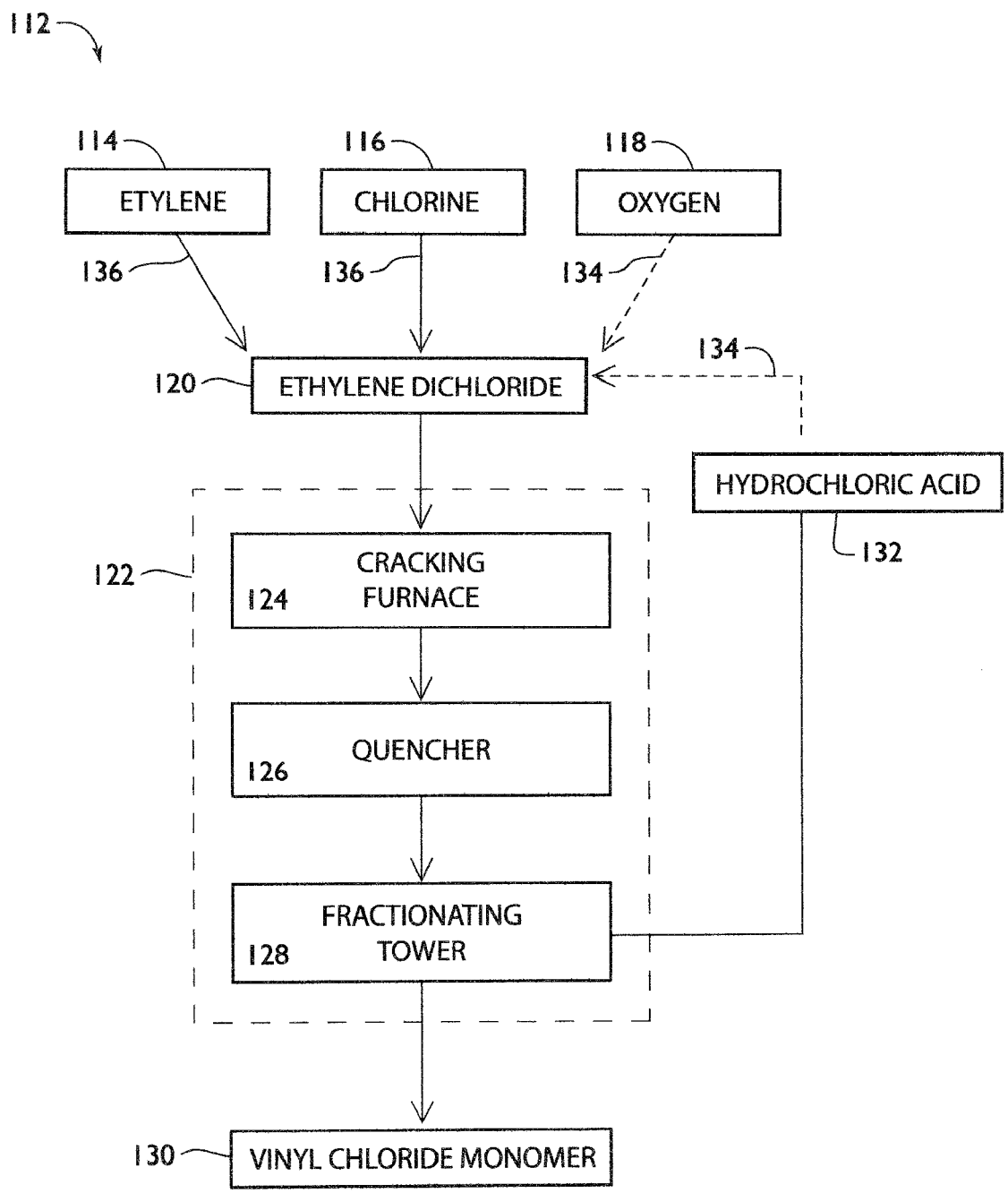
FIG. 1 is a block diagram demonstrating alternative processes to make vinyl chloride monomer according to the present invention.

The block diagram 112 of FIG. 1 details the process and apparatus for producing VCM from EDC. In the direct chlorination process 136, ethylene 114 and chlorine 116 are reacted together at 136 to form EDC 120. Alternatively or additionally, in the oxygen chlorination process 134, oxygen 118 is reacted with HCl 132, with steam, to form EDC 120. Vaporized EDC 120 is dried and typically passed over a catalyst packed in stainless steel tubes 14, shown in FIGS. 2 and 4A through 6C that are directly heated in a cracking furnace 124. The hot effluent gases are quenched in a quencher 126 and the condensed gases fed into a fractionating tower 128 operating under pressure to separate the product VCM 130 from HCl 132 and excess EDC, not shown in FIG. 1 but the excess EDC may be recycled in the same fashion as the HCl 132. The product VCM 130 is formed by condensing the vapors in a water condenser. The VCM 130 is then filtered and sent to either a storage tank for further processing to produce PVC or sold to other manufacturers that make PVC.

The overall reactions involved in the process of FIG. 1 are direct chlorination where $C_2H_4+Cl_2 \rightarrow C_2H_4Cl_2$, and oxygen chlorination where $C_2H_4+2HCl+\frac{1}{2}H_2O \rightarrow C_2H_4Cl_2+H_2O$. The reaction for the EDC cracking is $C_2H_4Cl_2 \rightarrow C_2H_3Cl + HCl$, where the excess HCl may optionally be recycled back into the oxygen chlorination reaction. The excess EDC may be recycled in either direct or oxygen chlorination processes.

Figure 2:
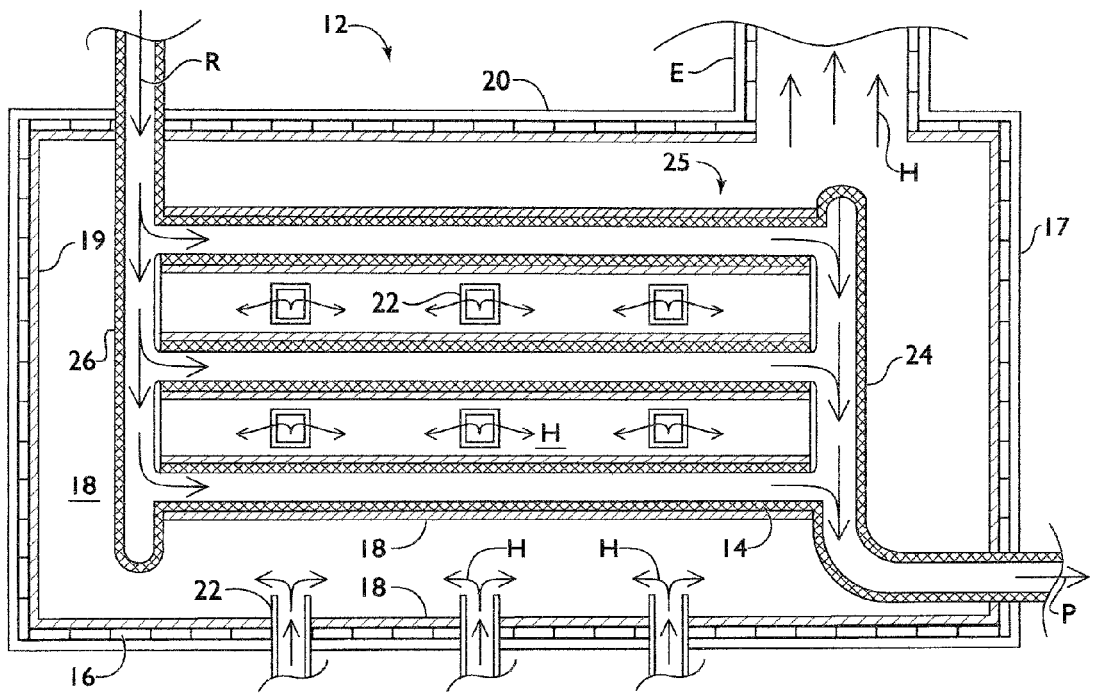
FIG. 2 is a schematic illustration of an embodiment of a cracking furnace having a thermal protective layer according to the present invention disposed on heat exposed surfaces thereof.

A cracking furnace 124 construction, as shown in FIG. 2, includes a firebox 12 defining a chamber 20 having walls 17, and containing a plurality of heat H generating burners 22 disposed within the firebox chamber 20, each wall 17 having an internal refractory surface 19 exposed to heat H generated by the burners 22. A tube structure 25 having at least one process tube 14 disposed within the firebox chamber 20, and in fluid communication therethrough, permitting fluid to pass through the firebox chamber 20 while the fluid therein is contained entirely within the tube structure 25. The term "fluid" as used herein includes both liquid and gas. Excess heat H is allowed to vent through an exhaust E. Each process tube 14 has an internal surface 21 defining an interior space, and an external surface 23 directly exposed to the heat H generated within the firebox chamber 20 for thermal communication through the process tube 14 to heat the fluid mixture therein. Each process tube 14, in this embodiment, extends from a first end 26 to a second end 24 allowing fluid communication therethrough. The EDC feedstock comprising is feed into the process tube structure 25 at the inlet R and the cracked product mixture is feed out to the quencher at P to form the VCM.

Figure 3A:
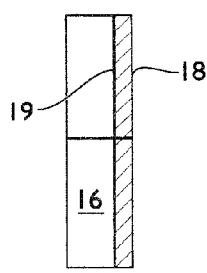
FIGS. 3a and 3b are side views of coated refractory brick according to an embodiment of the present invention.
Figure 4A:
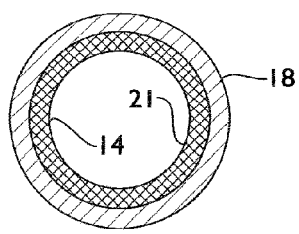
FIGS. 4a through 4c are cross sectional views of thermal protective layered process tubes according to alternative embodiments of the present invention.
Figure 4B:
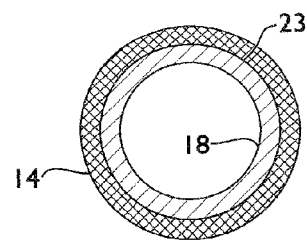
Figure 3B:
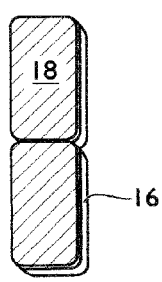
Figure 4C:
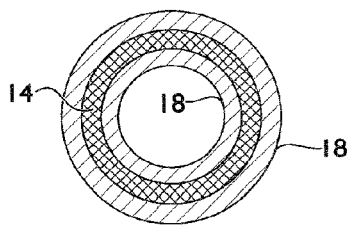

As shown in FIGS. 4a through 4c, a thermal protective layer 18 consisting of a high emissivity multifunctional nano coating disposed on the external surface 23 of the process tube 14, on the internal surface 21 of the process tube 14, or on combinations thereof. A thermal protective layer 18 may be disposed on at least a part of the internal surface 19 of the firebox chamber 20. In some firebox chambers 20, at least part of at least a refractory wall 17 is composed of a plurality of refractory bricks 16 disposed therein forming the internal surface 19 of the firebox chamber 20. In other firebox chambers, castable or ceramic fiber is used to form the refractory surface of the firebox chamber 20, as is well known in the art. The thermal protective layer 18 may be disposed upon the refractory bricks 16, as shown in FIGS. 3a and 3b, or on the surface of castable or ceramic fiber refractory walls.

Examples of refractory walls include Empire (trademark) S, which is a high duty dry press fireclay brick, Clipper (trademark), Korundal XD (trademark) and Insblok-19 available from A.P. Green Industries, Inc. (of Mexico, Mo.). An example of a ceramic fiber refractory includes Insboard 2300 LD also available form A.P. Green Industries, Inc. These refractory materials contains approximately 9.7% to 61.5% silica ($SiO_2$), 12.1% to 90.0% alumina ($Al_2O_3$), 0.2% to 1.7% iron oxide ($Fe_2O_3$), up to 27.7% lime (CaO), 0.1% to 0.4% magnesia (MgO), 2.0% to 6.3% titania ($TiO_2$) and 0.1% to 2.4% of alkalies ($Na_2O$ plus $K_2O$).

Figure 5A:
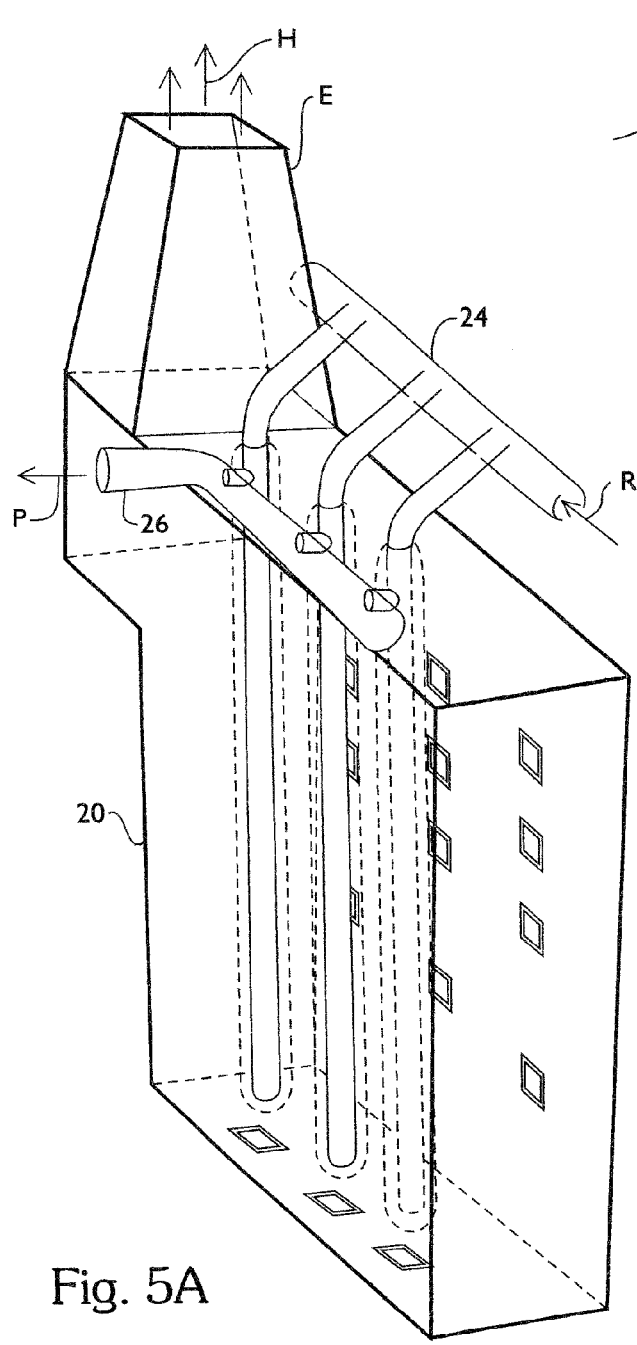
FIGS. 5a and 5b are schematic illustrations of an additional embodiment of a cracking furnace, utilizing a tube within a tube configuration, having a thermal protective layer according to the present invention disposed upon heat exposed surfaces thereof.
Figure 5B:
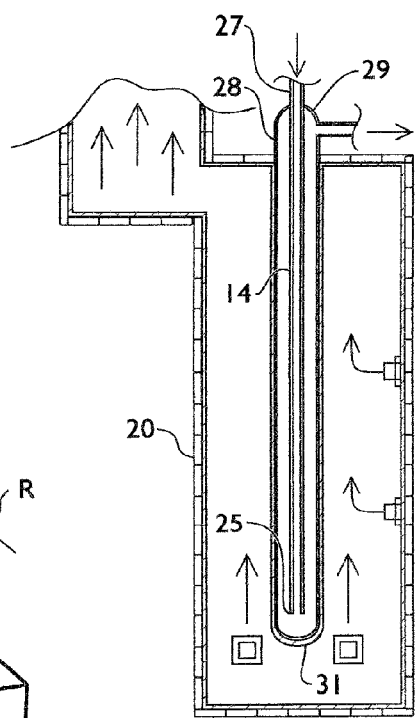
Figure 6A:
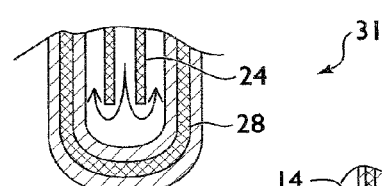
FIGS. 6a through 6c are sectional side views of emissivity coated process tubes according to the alternative embodiment of FIGS. 5a and 5b of the present invention.
Figure 6B:
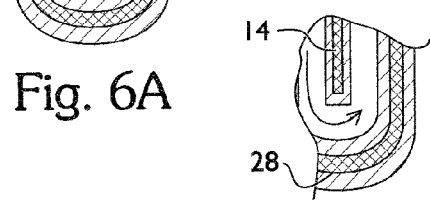
Figure 6C:
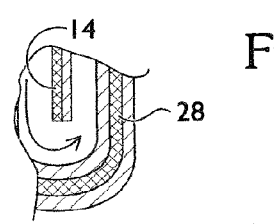

In an alternative cracking furnace construction 124, as shown in FIGS. 5a and 5b, a second process tube 28 is provided about the first process tube 14 and encompassing the first process tube 14 therein, as shown. The second process tube 28 have first and second ends 29 and 31, wherein the second end 31 is closed, as shown. A fluid entering through the first end 27 of the first thermal tube 14 is ejected out of an opening 25 dispose adjacent the first end 29 of the second thermal tube 28.

A conventional means for feeding the EDC containing feed stock fluid mixture R into the tube structure 25 adjacent the first end 24 wherein the feed stock fluid mixture flows through the interior space of each refractory tube 14 from first 24 through second ends 26, and is heated therein by thermal communication through the process tube 14, discharging a cracked hydrocarbon product containing VCM fluid mixture P out of the tube structure 25. A quencher 126 for receiving the cracked hydrocarbon product containing VCM fluid mixture when it is discharged from the tube structure 25 also is provided. Various tube 14 configurations exist but each define interior spaces and have internal and external surfaces thereof.

The thermal protective layer 18 may be applied as a high emissivity multifunctional thermal protective coating. Suitable coatings and methods of application are described in U.S. Pat. Nos. 7,105,047 and 6,921,431 and assigned to Wessex Incorporated, the contents of which are incorporated herein in their entirety.

A high emissivity coating suitable for forming a thermal protective layer on a metal/alloy process tube assembly of the present invention may contain from about 5% to about 30% of an inorganic adhesive, from about 45% to about 92% of a filler, and from about 1% to about 20% of one or more emissivity agents, in a dry admixture. Preferably, the dry admixture also contains from about 1% to about 5% of a stabilizer.

An alternative high emissivity coating suitable for forming a thermal protective layer on a ceramic process tubes and assembly, and on ceramic refractory wall materials, including brick, castable and ceramic fiber refractory walls, according to an embodiment of the present invention may contain from about 5% to about 35% of colloidal silica, from about 23% to about 79% of a filler, from about 1% to about 20% of one or more emissivity agents. Preferably, a thermal protective layer of the present invention also contains from about 1.5% to about 5.0% of a stabilizer.

As used herein, all percentages (%) are percent weight-to-weight, also expressed as weight/weight %, % (w/w), w/w, w/w % or simply %, unless otherwise indicated. Also, as used herein, the terms "wet admixture" refers to relative percentages of the composition of the thermal protective coating in solution and "dry admixture" refers to the relative percentages of the composition of the dry thermal protective coating mixture prior to the addition of water. In other words, the dry admixture percentages are those present without taking water into account. Wet admixture refers to the admixture in solution (with water). "Wet weight percentage" is the weight in a wet admixture, and "dry weight percentage" is the weight in a dry admixture without regard to the wet weight percentages. The term "total solids", as used herein, refers to the total sum of the silica/alumina and the alkali or ammonia ($NH_3$), plus the fraction of all solids including impurities. Weight of the solid component divided by the total mass of the entire solution, times one hundred, yields the percentage of "total solids".

Method of preparation of coating involves applying a wet admixture of the coating to the surface to be coated. Alternative methods may include spraying the wet admixture on the surface or atomizing the dry admixture and coating the surface accordingly.

In a coating solution according to the present invention, a wet admixture of the thermal protective coating, to be applied to metal/alloy process tubes/assembly, contains from about 6% to about 40% of an inorganic adhesive, from about 23% to about 46% of a filler, from about 0.5% to about 10% of one or more emissivity agents, and from about 18% to about 50% water. In order to extend the shelf life of the coating solution, from about 0.5% to about 2.5% of a stabilizer is preferably added to the wet admixture. The wet admixture coating solution contains between about 40% and about 60% total solids.

In a coating solution according to the present invention, a wet admixture of an alternative thermal protective coating, to be applied to the refractory structure and ceramic process tubes/assembly, contains from about 15% to about 45% of colloidal silica, from about 23% to about 55% of a filler, from about 0.5% to about 10% of one or more emissivity agents, from about 0.5% to about 2.5% of a stabilizer and from about 18% to about 40% water. The wet admixture coating solution contains between about 40% and about 70% total solids.

The inorganic adhesive is preferably an alkali/alkaline earth metal silicate taken from the group consisting of sodium silicate, potassium silicate, calcium silicate, and magnesium silicate. The colloidal silica is preferably a mono-dispersed distribution of colloidal silica, and therefore, has a very narrow range of particle sizes. The filler is preferably a metal oxide taken from the group consisting of silicon dioxide, aluminum oxide, titanium dioxide, magnesium oxide, calcium oxide and boron oxide. The emissivity agent(s) is preferably taken from the group consisting of silicon hexaboride, carbon tetraboride, silicon tetraboride, silicon carbide, molybdenum disilicide, tungsten disilicide, zirconium diboride, cupric chromite, and metallic oxides such as iron oxides, magnesium oxides, manganese oxides, copper chromium oxides, and chromium oxides, cerium oxides, and terbium oxides, and derivatives thereof. The copper chromium oxide, as used in the present invention, is a mixture of cupric chromite and cupric oxide. The stabilizer may be taken from the group consisting of bentonite, kaolin, magnesium alumina silica clay, tabular alumina and stabilized zirconium oxide. The stabilizer is preferably bentonite. Other ball clay stabilizers may be substituted herein as a stabilizer. Colloidal alumina, in addition to or instead of colloidal silica, may also be included in the admixture of the present invention. When colloidal alumina and colloidal silica are mixed together one or the other requires surface modification to facilitate mixing, as is known in the art.

Coloring may be added to the protective coating layer of the present invention to depart coloring to the tubes. Inorganic pigments may be added to the protective coating without generating toxic fumes. In general, inorganic pigments are divided into the subclasses: colored (salts and oxides), blacks, white and metallic. Suitable inorganic pigments include but are not limited to yellow cadmium, orange cadmium, red cadmium, deep orange cadmium, orange cadmium lithopone and red cadmium lithopone.

A preferred embodiment of the present invention contains a dry admixture of from about 10% to about 25% sodium silicate, from about 50% to about 79% silicon dioxide powder, and from about 4% to about 15% of one or more emittance agent(s) taken from the group consisting of iron oxide, boron silicide, boron carbide, silicon tetraboride, silicon carbide molybdenum disilicide, tungsten disilicide, zirconium diboride. Preferred embodiments of the thermal coating may contain from about 1.0% to about 5.0% bentonite powder in dry admixture. The corresponding coating in solution (wet admixture) for this embodiment contains from about 10.0% to about 35.0% sodium silicate, from about 25.0% to about 50.0% silicon dioxide, from about 18.0% to about 39.0% water, and from about 1.0% to about 8.5% one or more emittance agent(s). This wet admixture must be used immediately. In order to provide a coating solution admixture (wet admixture), which may be stored and used later, preferred embodiments of the thermal coating contain from about 0.25% to about 2.50% bentonite powder. Preferably deionized water is used. Preferred embodiments of the wet admixture have a total solids content ranging from about 45% to about 55%.

A preferred thermal protective coating of the present invention contains a dry admixture from about 15.0% to about 20.0% sodium silicate, from about 69.0% to about 79.0% silicon dioxide powder, about 1.00% bentonite powder, and from about 5.00% to about 15.0% of an emittance agent. The emittance agent is taken from one or more of the following: iron oxide, boron silicide, and boron carbide.

A most preferred wet admixture contains about 20.0% sodium silicate based on a sodium silicate solids content of about 37.45%, from about 34.5% to about 39.5% silicon dioxide powder, about 0.500% bentonite powder, and from about 2.50% to about 7.5% of an emittance agent, with the balance being water. The emittance agent is most preferably taken from the group consisting of iron oxide, boron silicide, and boron carbide (also known as, carbon tetraboride). Preferred embodiments include those where the emittance agent comprises about 2.50% iron oxide, about 2.50% to about 7.5% boron silicide, or from about 2.50% to about 7.50% boron carbide. The pH of a most preferred wet admixture according to the present invention is about 11.2.+−.1.0, the specific gravity is about 1.45.+−.0.05 and the total solids content is about 50.+−.0.3%.

A preferred embodiment of the present invention contains a dry admixture of from about 10.0% to about 30.0% colloidal silica, from about 50% to about 79% silicon dioxide powder, and from about 2% to about 15% of one or more emittance agent(s) taken from the group consisting of cerium oxide, boron silicide, boron carbide, silicon tetraboride, silicon carbide molybdenum disilicide, tungsten disilicide, zirconium diboride, and from about 1.5% to about 5.0% bentonite powder. The corresponding coating in solution (wet admixture) for this embodiment contains from about 20.0% to about 35.0% colloidal silica, from about 25.0% to about 55.0% silicon dioxide, from about 18.0% to about 35.0% water, and from about 2.0% to about 7.5% one or more emittance agent(s), and from about 0.50% to about 2.50% bentonite powder. Preferably deionized water is used. Preferred embodiments of the wet admixture have a total solids content ranging from about 50% to about 65%.

A most preferred thermal protective coating of the present invention contains a dry admixture from about 15.0% to about 25.0% colloidal silica, from about 68.0% to about 78.0% silicon dioxide powder, about 2.00% to about 4.00% bentonite powder, and from about 4.00% to about 6.00% of an emittance agent. The emittance agent is taken from one or more of the following: zirconium boride, boron silicide, and boron carbide.

A most preferred wet admixture contains about 27.0% colloidal silica based on a colloidal silica solids content of about 40%, from about 25% to about 50% silicon dioxide powder, about 1.50% bentonite powder, and from about 2.50% to about 5.50% of an emittance agent, with the balance being water. The emittance agent is most preferably taken from the group consisting of zirconium boride, boron silicide, and boron carbide. Preferred embodiments include those where the emittance agent comprises about 2.50% zirconium diboride, about 2.50% boron silicide, or from about 2.50% to about 7.50% boron carbide. The specific gravity of a most preferred wet admixture is about 1.40 to 1.50 and the total solids content is about 50% to 60%.

An inorganic adhesive, which may be used in the present invention, includes N (trademark) type sodium silicate that is available from the PQ Corporation (of Valley Forge, Pa.). Sodium silicates ($Na_2O.XSiO_2$) are metal oxides of silica. All soluble silicates can be differentiated by their ratio, defined as the weight proportion of silica to alkali ($SiO_2/Na_2O$). Ratio determines the physical and chemical properties of the coating. The glassy nature of silicates imparts strong and rigid physical properties to dried films or coatings. Silicates air dry to a specific moisture level, according to ambient temperature and relative humidity. Heating is necessary to take these films to complete dryness—a condition in which silicates become nearly insoluble. Reaction with other materials, such as aluminum or calcium compounds, will make the film coating completely insoluble. The N (trademark) type sodium silicate, as used in the examples below, has a weight ratio $SiO_2/Na_2O$ is 3.22, 8.9% $Na_2O$, 28.7% $SiO_2$, with a density (at room temperature of 20° C.) of 41.0°Be', 11.6 lb/gal or 1.38 g/cm$^3$. The pH is 11.3 with a viscosity of 180 centipoises. The N type sodium silicate is in a state of a syrupy liquid.

The term "total solids" refers to the sum of the silica and the alkali. The weight ratio is a most important silicate variable. Ratio determines the product solubility, reactivity and physical properties. Ratio is either the weight or molar proportion of silica to alkali. Density is an expression of total solids and is typically determined using a hydrometer or pycnometer Ludox (trademark) TM 50 colloidal silica and Ludox (trademark) AS 40 colloidal silica are available from Grace Davidson (of Columbia, Md.). The particles in Ludox (trademark) colloidal silica are discrete uniform spheres of silica which have no internal surface area or detectable crystallinity. Most are dispersed in an alkaline medium which reacts with the silica surface to produce a negative charge. Because of the negative charge, the particles repel one another resulting in stable products. Although most grades are stable between pH 8.5-11.0, some grades are stable in the neutral pH range. Ludox (trademark) colloidal silicas are aqueous colloidal dispersions of very small silica particles. They are opalescent to milky white liquids. Because of their colloidal nature, particles of Ludox (trademark) colloidal silica have a large specific surface area which accounts for the novel properties and wide variety of uses. Ludox (trademark) colloidal silica is available in two primary families: mono-dispersed, very narrow particle size distribution of Ludox (trademark) colloidal silica and poly-dispersed, broad particle size distribution of Ludox (trademark) P. The Ludox (trademark) colloidal silica is converted to a dry solid, usually by gelation. The colloidal silica can be gelled by (1) removing water, (2) changing pH, or (3) adding a salt or water-miscible organic solvent. During drying, the hydroxyl groups on the surface of the particles condense by splitting out water to form siloxane bonds (Si—O—Si) resulting in coalescence and interbonding. Dried particles of Ludox (trademark) colloidal silica are chemically inert and heat resistant. The particles develop strong adhesive and cohesive bonds and are effective binders for all types of granular and fibrous materials, especially when use at elevated temperature is required.

Colloidal alumina is available as Nyacol (trademark) colloidal alumina, and specifically, Nyacol (trademark) AL20, available from Nyacol Nano Technologies, Inc. (Ashland, Mass.), and is available in deionized water to reduce the sodium and chlorine levels to less than 10 ppm. It contains about 20 percent by weight of $AL_2O_3$, a particle size of 50 nm, positive particle charge, pH 4.0, specific gravity of 1.19, and a viscosity of 10 cPs.

The filler may be a silicon dioxide powder such as Min-U-Sil (trademark) 5 silicon dioxide available from U.S. Silica (of Berkeley Springs, W. Va.). This silicon dioxide is fine ground silica. Chemical analysis of the Min-U-Sil (trademark) silicon dioxide indicates contents of 98.5% silicon dioxide, 0.060% iron oxide, 1.1% aluminum oxide, 0.02% titanium dioxide, 0.04% calcium oxide, 0.03% magnesium oxide, 0.03% sodium dioxide, 0.03% potassium oxide and a 0.4% loss on ignition. The typical physical properties are a compacted bulk density of 41 lbs/ft.sup.3, an uncompacted bulk density of 36 lbs/ft$^3$, a hardness of 7 Mohs, hegman of 7.5, median diameter of 1.7 microns, an oil absorption (D-1483) of 44, a pH of 6.2, 97%−5 microns, 0.005%+325 Mesh, a reflectance of 92%, a 4.2 yellowness index and a specific gravity of 2.65.

Emittance agents are available from several sources. Emissivity is the relative power of a surface to absorb and emit radiation, and the ratio of the radiant energy emitted by a surface to the radiant energy emitted by a blackbody at the same temperature. Emittance is the energy reradiated by the surface of a body per unit area.

The boron carbide, also known as carbon tetraboride, which may be used as an emissivity agent in the present invention, is sold as 1000 W boron carbide and is available from Electro Abrasives (of Buffalo, N.Y.). Boron Carbide is one of the hardest man made materials available. Above 1300° C., it is even harder than diamond and cubic boron nitride. It has a four point flexural strength of 50,000 to 70,000 psi and a compressive strength of 414,000 psi, depending on density. Boron Carbide also has a low thermal conductivity (29 to 67 W/mK) and has electrical resistivity ranging from 0.1 to 10 ohm-cm. Typical chemical analysis indicates 77.5% boron, 21.5% carbon, iron 0.2% and total Boron plus Carbon is 98%. The hardness is 2800 Knoop and 9.6 Mohs, the melting point is 4262° F. (2350° C.), the oxidation temperature is 932° F. (500° C.), and the specific gravity is 2.52 g/cc.

1000 W green silicon carbide (SiC), an optional emissivity agent, is also available from Electro Abrasives. Green Silicon Carbide is an extremely hard (Knoop 2600 or Mohs 9.4) man made mineral that possesses high thermal conductivity (100 W/m-K). It also has high strength at elevated temperatures (at 1100° C., Green SiC is 7.5 times stronger than $Al_2O_3$). Green SiC has a Modulus of Elasticity of 410 GPa, with no decrease in strength up to 1600° C., and it does not melt at normal pressures but instead dissociates at 2815.5° C. Green silicon carbide is a batch composition made from silica sand and coke, and is extremely pure. The physical properties are as follows for green silicon carbide: the hardness is 2600 Knoop and 9.4 Mohs, the melting point is 4712° F. (2600° C.), and the specific gravity is 3.2 g/cc. The typical chemical analysis is 99.5% SiC, 0.2% $SiO_2$, 0.03% total Si, 0.04% total Fe, and 0.1% total C. Commercial silicon carbide and molybdenum disilicide may need to be cleaned, as is well known in the art, to eliminate flammable gas generated during production.

Boron silicide ($B_6Si$) (Item # B-1089) is available from Cerac (of Milwaukee, Wis.). The boron silicide, also known as silicon hexaboride, available from Cerac has a −200 mesh (about 2 microns average) and a typical purity of about 98%. Zirconium boride ($ZrB_2$) is also available from Cerac with a typical average of 10 microns or less (−325 mesh), and a typical purity of about 99.5%.

Iron oxide available from Hoover Color (of Hiwassee, Va.) is a synthetic black iron oxide ($Fe_2O_3$) which has an iron oxide content of 60%, a specific gravity of 4.8 gm/cc, a tap density (also known as, bulk density) of 1.3 gm/cc, oil absorption of 15 lbs/100 lbs, a 325 mesh residue of 0.005, and a pH ranging from 7 to 10.

Preferably the admixture of the present invention includes bentonite powder, tabular alumina, or magnesium alumina silica clay. The bentonite powder permits the present invention to be prepared and used at a later date. Preparations of the present invention without bentonite powder must be used immediately. The examples provided for the present invention include PolarGel bentonite powder are available from Mineral and Pigment Solutions, Inc. (of South Plainfield, N.J.). Technical grade bentonite is generally used for the purpose of suspending, emulsifying and binding agents, and as Theological modifiers. The typical chemical analysis 59.00% to 61.00% of silicon dioxide ($SiO_2$), 20.00% to 22.00% of aluminum oxide ($Al_2O_3$), 2.00% to 3.00% calcium oxide (CaO), 3.50% to 4.30% magnesium oxide (MgO), 0.60% to 0.70% ferric oxide ($Fe_2O_3$), 3.50% to 4.00% sodium oxide ($Na_2O$), 0.02% to 0.03% potassium oxide ($K_2O$), and 0.10% to 0.20% titanium dioxide and a maximum of 8.0% moisture. The pH value ranges from 9.5 to 10.5. Typical physical properties are 83.0 to 87.0 dry brightness, 2.50 to 2.60 specific gravity, 20.82 pounds/solid gallon, 0.0480 gallons for one pound bulk, 24 ml minimum swelling power, maximum 2 ml gel formation, and 100.00% thru 200 mesh. Tabular alumina (Alumina Tab T64 Item 635) and magnesium alumina silica clay (Mag Alum Sil Technical Item 105) are also available from Mineral and Pigment Solutions, Inc.

The admixture of the present invention preferably includes bentonite powder, tabular alumina, or other magnesium alumina silica clay as the stabilizer. The bentonite powder permits the present invention to be prepared and used at a later date. The examples provided for the present invention include PolarGel bentonite powder (Item #354) available from Mineral and Pigment Solutions, Inc. (of South Plainfield, N.J.). Bentonite is generally used for the purpose of suspending, emulsifying and binding agents, and as rheological modifiers. The typical chemical analysis is 59.00% to 61.00% of silicon dioxide ($SiO_2$), 20.00% to 22.00% of aluminum oxide ($Al_2O_3$), 2.00% to 3.00% calcium oxide (CaO), 3.50% to 4.30% magnesium oxide (MgO), 0.60% to 0.70% ferric oxide ($Fe_2O_3$), 3.50% to 4.00% sodium oxide ($Na_2O$), 0.02% to 0.03% potassium oxide ($K_2O$), and 0.10% to 0.20% titanium dioxide and a maximum of 8.0% moisture. The pH value ranges from 9.5 to 10.5. Typical physical properties are 83.0 to 87.0 dry brightness, 2.50 to 2.60 specific gravity, 20.82 pounds/solid gallon, 0.0480 gallons for one pound bulk, 24 ml minimum swelling power, maximum 2 ml gel formation, and 100.00% thru 200 mesh. Tabular alumina (Alumina Tab T64 Item 635) and magnesium alumina silica clay (Mag Alum Sil Technical Item 105) are also available from Mineral and Pigment Solutions, Inc.

Colorants, which may be added to the present invention, include but are not limited to inorganic pigments. Suitable inorganic pigments, such as yellow iron oxide, chromium oxide green, red iron oxide, black iron oxide, titanium dioxide, are available from Hoover Color Corporation. Additional suitable inorganic pigments, such as copper chromite black spinel, chromium green-black hematite, nickel antimony titanium yellow rutile, manganese antimony titanium buff rutile, and cobalt chromite blue-green spinel, are available from The Shepherd Color Company (of Cincinnati, Ohio).

A surfactant may be added to the wet admixture prior to applying the thermal protective layer to the support layer. The surfactant was surfyonol (trademark) 465 surfactant available from Air Products and Chemicals, Inc. (of Allentown, Pa.). The surfyonol (trademark) has a chemical structure of ethoxylated 2,4,7,9-tetramethyl 5 decyn-4,7-diol. Other surfactants may be used, such as STANDAPOL (trademark) T, INCI which has a chemical structure of triethanolamine lauryl sulfate, liquid mild primary surfactant available from Cognis-Care Chemicals (of Cincinnati, Ohio). The amount of surfactant present by weight in the wet admixture in from about 0.05% to about 0.2%.

The thermal protective coating is applied to the surface to form a thermal protective layer. The substrate surface may be a metallic substrate such as iron, aluminum, alloys, steel, cast iron, stainless steel and the like, or it may be a ceramic surface, as is well known in the art. The coating is typically applied wet, and either allowed to air dry or heat dry.

Surface preparation for metal or ceramic structures are similar. The surface should be clear of all dirt, loose material, surfactants, oils, gasses, etc. A metal surface may be grit blasted. Grit blasting is desirable to remove oxidation and other contaminants for metal surfaces only. Grits media should be sharp particles. Gun pressure will vary depending on the cut type, condition of the metal and profile desired. Very old metal will require 70-80 psi. Oil and water-free compressed air is required. Proper filters for the removal of oil and water are required. Other alkaline type metal cleanses may also be utilized.

After the grit blast, the surface should be thoroughly cleaned to remove all loose particles with clean oil and water free air blasts. Avoid contaminating surface with fingerprints. Acetone can be used (under proper ventilation and exercising all necessary precautions when working with acetone) on a clean cloth to wipe the surface clean. A cleaning compound may be used on certain stainless steel in lieu of grit blasting. Durlum available from Blue Wave Ultrasonics (of Davenport, Iowa), a powdered alkaline cleaner, may be used in cleaning metal surface, When using the wet admixture containing a stabilizer, solids may settle during shipment or storage. Prior to use all previously mixed coating must be thoroughly re-mixed to ensure all settled solids and clumps are completely re-dispersed. When not using a stabilizer, the coating may not be stored for any period of time. In any case, the coating should be used immediately after mixing to minimize settling.

Mixing instructions for one and five gallon containers. High speed/high shear saw tooth dispersion blade 5" diameter for one gallon containers and 7" diameter for five gallon containers may be attached to a hand drill of sufficient power with a minimum no load speed of 2000 rpm shear. Dispersion blades can be purchased from numerous suppliers Mix at high speed to ensure complete re-dispersion for a minimum of 30 minutes.

The product should be applied directly after cleaning a metal surface so minimal surface oxidation occurs. The product should be applied in a properly ventilated and well lit area, or protective equipment should be used appropriate to the environment, for example within a firebox. The mixed product should not be filtered or diluted.

A high volume low pressure (HVLP) spray gun should be used with 20-40 psi of clean, oil and water free air. Proper filters for removal of oil and water are required. Alternatively, an airless spray gun may be used. Other types of spray equipment may be suitable. The applicator should practice spraying on scrap metal prior to spraying the actual part to ensure proper coverage density. An airless spray system is preferable for applications on ceramic surfaces such as the refractory materials. Suitable airless spray systems are available from Graco (of Minneapolis, Minn.). Suitable HVLP spray systems, which are desirable for metal/alloy process tubes, are available from G.H. Reed Inc. (of Hanover, Pa.). A high speed agitator may be desirable. Suitable spray gun tips may be selected to provide the proper thickness without undue experimentation.

Controlling the coverage density may be critical to coating performance. The thermal layer thickness should be from about two (2) mils (about 50 microns ($\mu$)) to about ten (10) mils (about 255$\mu$), depending upon typed, size and condition of substrate. One (1) mil equals 25.4$\mu$. Proper thickness may vary. If possible, rotate the part 90 degrees at least once to maintain even coverage, Allow 1 to 4 hours of dry time before the part is handled, depending upon humidity and temperature.

An example of the present invention was carried out using a VCM furnace with a production of 40,000 pounds per hour, natural gas fuel type, an annual usage of 450,000 MMBTU, with furnace controls that are programmable logic controls controlled by heat distribution in firebox. The VCM furnace had aged fire brick and metal incoloy tubes that were coated with a thermal protective coating according to the present invention. The EDC is cracked at 1400° F. to 1450° F. The coated VCM furnace performed with exceptional results within days of activation. Initial energy savings were instantaneously 7% with no furnace adjustments, along with a production increase.

A VCM furnace containing aged fire brick with a thermal protective layer thereon. The thermal protective layer contained 15.0% sodium silicate, 79.0% silicon dioxide powder, 5.0% boron carbide, and 1.0% bentonite powder. The thermal protective layer was applied to aged fire brick as a thermal protective coating containing 20.0% sodium silicate, 39.5% silicon dioxide powder, 2.5% boron carbide, 0.50% bentonite powder, and 37.5% deionized water.

The metal incoloy tubes were coated with with a thermal protective layer thereon. The thermal protective layer contained 16.5% colloidal silica, 76.3% silicon dioxide powder, 4.3% silicon hexaboride, and 2.9% bentonite powder. The thermal protective layer was applied to the tubes as a thermal protective coating containing 26.81% colloidal silica, 49.60% silicon dioxide powder, 2.80% silicon hexaboride, 1.88% bentonite powder, and 18.91% deionized water.

The resulting improvements noted included a greater than 10% production increase, energy savings greater than 5%, improved cracking reaction in the process tubes, improved thermal response, steam savings for preproduction product heating, reduced maintenance and downtime, furnace skin temperature reduces more then 20% and reduced air emissions. The estimated economic savings include a fuel savings of three percent with a production increase of then percent. The tube life expected to double from five to ten years. The resultant expected reduction in downtime and product cracking improvement should add to the savings.

It is to be understood that the present invention is not limited to the embodiments described above, but encompasses any and all embodiments within the scope of the following claims.

What is claimed is:

1. A process of manufacturing vinyl chloride monomers, comprising:
   cracking an ethylene dichloride feedstock in a pyrolysis furnace by feeding the feedstock through at least one heated process tube having first and second ends with an internal surface defining an interior space having a thermal protective layer disposed thereon, the thermal protective layer containing
   a. from about 5% to about 30% of an inorganic adhesive, from about 45% to about 92% of a filler, and from about 1% to about 20% of one or more emissivity agents, or
   b. from about 5% to about 35% of colloidal silica, colloidal alumina, or combinations thereof; from about 23% to about 79% of a filler, from about 1% to about 20% of one or more emissivity agents.

2. The process of claim 1, wherein:
   the pyrolysis furnace comprises a firebox chamber having refractory walls with exposed surfaces, and a plurality of heat generating burners; and the at least one process tubes are disposed in a process tube structure disposed within the firebox chamber, and in fluid communication therethrough, permitting feedstock to pass through the firebox chamber while fluidly contained solely within the process tube structure, and an external surface directly exposed to heat generated within the firebox chamber for thermal communication therethrough wherein a thermal protective layer consisting of a high emissivity coating is disposed on the external surface of the process tubes, on the exposed surfaces of the refractory walls, or combinations thereof, wherein the thermal protective layer contains a. from about 5% to about 30% of an inorganic adhesive, from about 45% to about 92% of a filler, and from about 1% to about 20% of one or more emissivity agents, or b. from about 5% to about 35% of colloidal silica, colloidal alumina, or combinations thereof; from about 23% to about 79% of a filler, from about 1% to about 20% of one or more emissivity agents.

3. The process of claim 1, wherein:

the thermal protective layer further comprises from about 1.0% to about 5.0% of a stabilizer;

the thermal protective layer further comprises a surfactant;

the thermal protective layer further comprises a colorant;

the inorganic adhesive is taken from the group consisting of an alkali/alkaline earth metal silicate taken from the group consisting of sodium silicate, potassium silicate, calcium silicate, and magnesium silicate;

the filler is taken from the group consisting of silicon dioxide, aluminum oxide, titanium dioxide, magnesium oxide, calcium oxide, and boron oxide;

the one or more emissivity agents are taken from the group consisting of silicon hexaboride, boron carbide, silicon tetraboride, silicon carbide, molybdenum disilicide, tungsten disilicide, zirconium diboride, cupric chromite, and metallic oxides; or combinations thereof;

the stabilizer is taken from the group consisting of bentonite, kaolin, magnesium alumina silica clay, tabular alumina, and stabilized zirconium oxide;

the thermal protective layer is from about two (2) mils (about 50 microns (0) to about ten (10) mils (about 255 μl) thick; or combinations thereof.

4. The process of claim 1, wherein:

a thermal protective layer contains a. from about 5% to about 30% of an inorganic adhesive, the inorganic adhesive is taken from the group consisting of an alkali/alkaline earth metal silicate taken from the group consisting of sodium silicate, potassium silicate, calcium silicate, and magnesium silicate; from about 45% to about 92% of a filler, the filler taken from the group consisting of silicon dioxide, aluminum oxide, titanium dioxide, magnesium oxide, calcium oxide, and boron oxide; and from about 1% to about 20% of one or more emissivity agents taken from the group consisting of silicon hexaboride, boron carbide, silicon tetraboride, silicon carbide, molybdenum disilicide, tungsten disilicide, zirconium diboride, cupric chromite, and metallic oxides;

b. from about 5% to about 35% of colloidal silica, colloidal alumina, or combinations thereof; from about 23% to about 79% of a filler taken from the group consisting of silicon dioxide, aluminum oxide, titanium dioxide, magnesium oxide, calcium oxide, and boron oxide; and from about 1% to about 20% of one or more emissivity agents taken from the group consisting of silicon hexaboride, boron carbide, silicon tetraboride, silicon carbide, molybdenum disilicide, tungsten disilicide, zirconium diboride, cupric chromite, and metallic oxides;

c. from about 5% to about 30% of an inorganic adhesive, the inorganic adhesive is taken from the group consisting of an alkali/alkaline earth metal silicate taken from the group consisting of sodium silicate, potassium silicate, calcium silicate, and magnesium silicate; from about 45% to about 92% of a filler, the filler taken from the group consisting of silicon dioxide, aluminum oxide, titanium dioxide, magnesium oxide, calcium oxide, and boron oxide; and from about 1% to about 20% of one or more emissivity agents taken from the group consisting of silicon hexaboride, boron carbide, silicon tetraboride, silicon carbide, molybdenum disilicide, tungsten disilicide, zirconium diboride, cupric chromite, and metallic oxides; and from about 1% to about 5% of a stabilizer taken from the group consisting of bentonite, kaolin, magnesium alumina silica clay, tabular alumina, and stabilized zirconium oxide; or d. from about 5% to about 35% of colloidal silica, colloidal alumina, or combinations thereof; from about 23% to about 79% of a filler taken from the group consisting of silicon dioxide, aluminum oxide, titanium dioxide, magnesium oxide, calcium oxide, and boron oxide; and from about 1% to about 20% of one or more emissivity agents taken from the group consisting of silicon hexaboride, boron carbide, silicon tetraboride, silicon carbide, molybdenum disilicide, tungsten disilicide, zirconium diboride, cupric chromite, and metallic oxides; and from about 1.5% to about 5.0% of a stabilizer taken from the group consisting of bentonite, kaolin, magnesium alumina silica clay, tabular alumina, and stabilized zirconium oxide.

5. The process of claim 1, wherein:

a thermal protective layer contains a. from about 10% to about 30% sodium silicate, from about 50% to about 79% silicon dioxide powder, and from about 4% to about 15% of one or more emissivity agents taken from the group consisting of iron oxide, boron silicide, boron carbide, silicon tetraboride, silicon carbide powder, molybdenum disilicide, tungsten disilicide, and zirconium diboride;

b. from about 10% to about 30% sodium silicate, from about 50% to about 79% silicon dioxide powder, from about 4% to about 15% of one or more emissivity agents taken from the group consisting of iron oxide, boron silicide, boron carbide, silicon tetraboride, silicon carbide powder, molybdenum disilicide, tungsten disilicide, and zirconium diboride, and from about 1% to about 5% of a stabilizer taken from the group consisting of bentonite, kaolin, magnesium alumina silica clay, tabular alumina, and stabilized zirconium oxide;

c. from about 10% to about 30% colloidal silica, from about 50% to about 79% silicon dioxide powder, and from about 2% to about 15% of one or more emissivity agents taken from the group consisting of iron oxide, boron silicide, boron carbide, silicon tetraboride, silicon carbide molybdenum disilicide, tungsten disilicide, and zirconium diboride; or d. from about 10% to about 30% colloidal silica, from about 50% to about 79% silicon dioxide powder, from about 2% to about 15% of one or more emissivity agents taken from the group consisting of iron oxide, boron silicide, boron carbide, silicon tetraboride, silicon carbide molybdenum disilicide, tungsten disilicide, and zirconium diboride, and from about 1.5% to about 5.0% of a stabilizer taken from the group consisting of bentonite, kaolin, magnesium alumina silica clay, tabular alumina, and stabilized zirconium oxide.

6. The process of claim 1, wherein:
a second thermal process tube is provided about the first thermal process tube encompassing the first thermal process tube therein
the thermal process tube having first and second ends, wherein the second end is closed;
such that a fluid entering through the first end of the first thermal tube is ejected out of an opening dispose adjacent the first end of the second thermal tube.

7. The process of claim 2, wherein:
the thermal protective layer further comprises from about 1.0% to about 5.0% of a stabilizer;
the thermal protective layer further comprises a surfactant;
the thermal protective layer further comprises a colorant;
the inorganic adhesive is taken from the group consisting of an alkali/alkaline earth metal silicate taken from the group consisting of sodium silicate, potassium silicate, calcium silicate, and magnesium silicate;
the filler is taken from the group consisting of silicon dioxide, aluminum oxide, titanium dioxide, magnesium oxide, calcium oxide, and boron oxide;
the one or more emissivity agents are taken from the group consisting of silicon hexaboride, boron carbide, silicon tetraboride, silicon carbide, molybdenum disilicide, tungsten disilicide, zirconium diboride, cupric chromite, and metallic oxides; or combinations thereof;
the stabilizer is taken from the group consisting of bentonite, kaolin, magnesium alumina silica clay, tabular alumina, and stabilized zirconium oxide;
the thermal protective layer is from about two (2) mils (about 50 microns (0) to about ten (10) mils (about 255 μl) thick; or
combinations thereof.

8. The process of claim 2, wherein:
a thermal protective layer contains
a. from about 5% to about 30% of an inorganic adhesive, the inorganic adhesive is taken from the group consisting of an alkali/alkaline earth metal silicate taken from the group consisting of sodium silicate, potassium silicate, calcium silicate, and magnesium silicate; from about 45% to about 92% of a filler, the filler taken from the group consisting of silicon dioxide, aluminum oxide, titanium dioxide, magnesium oxide, calcium oxide, and boron oxide; and from about 1% to about 20% of one or more emissivity agents taken from the group consisting of silicon hexaboride, boron carbide, silicon tetraboride, silicon carbide, molybdenum disilicide, tungsten disilicide, zirconium diboride, cupric chromite, and metallic oxides;
b. from about 5% to about 35% of colloidal silica, colloidal alumina, or combinations thereof; from about 23% to about 79% of a filler taken from the group consisting of silicon dioxide, aluminum oxide, titanium dioxide, magnesium oxide, calcium oxide, and boron oxide; and from about 1% to about 20% of one or more emissivity agents taken from the group consisting of silicon hexaboride, boron carbide, silicon tetraboride, silicon carbide, molybdenum disilicide, tungsten disilicide, zirconium diboride, cupric chromite, and metallic oxides;
c. from about 5% to about 30% of an inorganic adhesive, the inorganic adhesive is taken from the group consisting of an alkali/alkaline earth metal silicate taken from the group consisting of sodium silicate, potassium silicate, calcium silicate, and magnesium silicate; from about 45% to about 92% of a filler, the filler taken from the group consisting of silicon dioxide, aluminum oxide, titanium dioxide, magnesium oxide, calcium oxide, and boron oxide; and from about 1% to about 20% of one or more emissivity agents taken from the group consisting of silicon hexaboride, boron carbide, silicon tetraboride, silicon carbide, molybdenum disilicide, tungsten disilicide, zirconium diboride, cupric chromite, and metallic oxides; and from about 1% to about 5% of a stabilizer taken from the group consisting of bentonite, kaolin, magnesium alumina silica clay, tabular alumina, and stabilized zirconium oxide; or
d. from about 5% to about 35% of colloidal silica, colloidal alumina, or combinations thereof; from about 23% to about 79% of a filler taken from the group consisting of silicon dioxide, aluminum oxide, titanium dioxide, magnesium oxide, calcium oxide, and boron oxide; and from about 1% to about 20% of one or more emissivity agents taken from the group consisting of silicon hexaboride, boron carbide, silicon tetraboride, silicon carbide, molybdenum disilicide, tungsten disilicide, zirconium diboride, cupric chromite, and metallic oxides; and from about 1.5% to about 5.0% of a stabilizer taken from the group consisting of bentonite, kaolin, magnesium alumina silica clay, tabular alumina, and stabilized zirconium oxide.

9. The process of claim 2, wherein:
a thermal protective layer contains
a. from about 10% to about 30% sodium silicate, from about 50% to about 79% silicon dioxide powder, and from about 4% to about 15% of one or more emissivity agents taken from the group consisting of iron oxide, boron silicide, boron carbide, silicon tetraboride, silicon carbide powder, molybdenum disilicide, tungsten disilicide, and zirconium diboride;
b. from about 10% to about 30% sodium silicate, from about 50% to about 79% silicon dioxide powder, from about 4% to about 15% of one or more emissivity agents taken from the group consisting of iron oxide, boron silicide, boron carbide, silicon tetraboride, silicon carbide powder, molybdenum disilicide, tungsten disilicide, and zirconium diboride, and from about 1% to about 5% of a stabilizer taken from the group consisting of bentonite, kaolin, magnesium alumina silica clay, tabular alumina, and stabilized zirconium oxide;
c. from about 10% to about 30% colloidal silica, from about 50% to about 79% silicon dioxide powder, and from about 2% to about 15% of one or more emissivity agents taken from the group consisting of iron oxide, boron silicide, boron carbide, silicon tetraboride, silicon carbide molybdenum disilicide, tungsten disilicide, and zirconium diboride; or
d. from about 10% to about 30% colloidal silica, from about 50% to about 79% silicon dioxide powder, from about 2% to about 15% of one or more emissivity agents taken from the group consisting of iron oxide, boron silicide, boron carbide, silicon tetraboride, silicon carbide molybdenum disilicide, tungsten disilicide, and zirconium diboride, and from about 1.5% to about 5.0% of a stabilizer taken from the group consisting of bentonite, kaolin, magnesium alumina silica clay, tabular alumina, and stabilized zirconium oxide.

10. The process of claim 2, wherein:
a second thermal process tube is provided about the first thermal process tube encompassing the first thermal process tube therein the thermal process tube having first and second ends, wherein the second end is closed;

such that a fluid entering through the first end of the first thermal tube is ejected out of an opening dispose adjacent the first end of the second thermal tube.

11. A process of manufacturing vinyl chloride monomers, comprising:

cracking an ethylene dichloride feedstock in a pyrolysis furnace by feeding the feedstock through at least one heated process tube having first and second ends, the pyrolysis furnace comprises a firebox chamber having refractory walls with exposed surfaces, and a plurality of heat generating burners; and the at least one process tubes are disposed in a process tube structure within the firebox chamber, and in fluid communication therethrough, permitting the feedstock to pass through the firebox chamber while fluidly contained solely within the process tube structure, and an external surface directly exposed to heat generated within the firebox chamber for thermal communication therethrough wherein a thermal protective layer consisting of a high emissivity coating is disposed on the internal surface of the process tubes, or on the external surface of the process tubes, or combinations thereof, wherein the thermal protective layer contains
  a. from about 5% to about 30% of an inorganic adhesive, from about 45% to about 92% of a filler, and from about 1% to about 20% of one or more emissivity agents, or
  b. from about 5% to about 35% of colloidal silica, colloidal alumina, or combinations thereof; from about 23% to about 79% of a filler, from about 1% to about 20% of one or more emissivity agents.

12. The process of claim 11, wherein:
the thermal protective layer further comprises from about 1.0% to about 5.0% of a stabilizer;
the thermal protective layer further comprises a surfactant;
the thermal protective layer further comprises a colorant;
the inorganic adhesive is taken from the group consisting of an alkali/alkaline earth metal silicate taken from the group consisting of sodium silicate, potassium silicate, calcium silicate, and magnesium silicate;
the filler is taken from the group consisting of silicon dioxide, aluminum oxide, titanium dioxide, magnesium oxide, calcium oxide, and boron oxide;
the one or more emissivity agents are taken from the group consisting of silicon hexaboride, boron carbide, silicon tetraboride, silicon carbide, molybdenum disilicide, tungsten disilicide, zirconium diboride, cupric chromite, and metallic oxides; or combinations thereof;
the stabilizer is taken from the group consisting of bentonite, kaolin, magnesium alumina silica clay, tabular alumina, and stabilized zirconium oxide;
the thermal protective layer is from about two (2) mils (about 50 microns (0) to about ten (10) mils (about 255μ) thick; or
combinations thereof.

13. The process of claim 11, wherein:
a thermal protective layer contains
  a. from about 5% to about 30% of an inorganic adhesive, the inorganic adhesive is taken from the group consisting of an alkali/alkaline earth metal silicate taken from the group consisting of sodium silicate, potassium silicate, calcium silicate, and magnesium silicate; from about 45% to about 92% of a filler, the filler taken from the group consisting of silicon dioxide, aluminum oxide, titanium dioxide, magnesium oxide, calcium oxide, and boron oxide; and from about 1% to about 20% of one or more emissivity agents taken from the group consisting of silicon hexaboride, boron carbide, silicon tetraboride, silicon carbide, molybdenum disilicide, tungsten disilicide, zirconium diboride, cupric chromite, and metallic oxides;
  b. from about 5% to about 35% of colloidal silica, colloidal alumina, or combinations thereof; from about 23% to about 79% of a filler taken from the group consisting of silicon dioxide, aluminum oxide, titanium dioxide, magnesium oxide, calcium oxide, and boron oxide; and from about 1% to about 20% of one or more emissivity agents taken from the group consisting of silicon hexaboride, boron carbide, silicon tetraboride, silicon carbide, molybdenum disilicide, tungsten disilicide, zirconium diboride, cupric chromite, and metallic oxides;
  c. from about 5% to about 30% of an inorganic adhesive, the inorganic adhesive is taken from the group consisting of an alkali/alkaline earth metal silicate taken from the group consisting of sodium silicate, potassium silicate, calcium silicate, and magnesium silicate; from about 45% to about 92% of a filler, the filler taken from the group consisting of silicon dioxide, aluminum oxide, titanium dioxide, magnesium oxide, calcium oxide, and boron oxide; and from about 1% to about 20% of one or more emissivity agents taken from the group consisting of silicon hexaboride, boron carbide, silicon tetraboride, silicon carbide, molybdenum disilicide, tungsten disilicide, zirconium diboride, cupric chromite, and metallic oxides; and from about 1% to about 5% of a stabilizer taken from the group consisting of bentonite, kaolin, magnesium alumina silica clay, tabular alumina, and stabilized zirconium oxide; or
  d. from about 5% to about 35% of colloidal silica, colloidal alumina, or combinations thereof; from about 23% to about 79% of a filler taken from the group consisting of silicon dioxide, aluminum oxide, titanium dioxide, magnesium oxide, calcium oxide, and boron oxide; and from about 1% to about 20% of one or more emissivity agents taken from the group consisting of silicon hexaboride, boron carbide, silicon tetraboride, silicon carbide, molybdenum disilicide, tungsten disilicide, zirconium diboride, cupric chromite, and metallic oxides; and from about 1.5% to about 5.0% of a stabilizer taken from the group consisting of bentonite, kaolin, magnesium alumina silica clay, tabular alumina, and stabilized zirconium oxide.

14. The process of claim 11, wherein:
a thermal protective layer contains
  a. from about 10% to about 30% sodium silicate, from about 50% to about 79% silicon dioxide powder, and from about 4% to about 15% of one or more emissivity agents taken from the group consisting of iron oxide, boron silicide, boron carbide, silicon tetraboride, silicon carbide powder, molybdenum disilicide, tungsten disilicide, and zirconium diboride;
  b. from about 10% to about 30% sodium silicate, from about 50% to about 79% silicon dioxide powder, from about 4% to about 15% of one or more emissivity agents taken from the group consisting of iron oxide, boron silicide, boron carbide, silicon tetraboride, silicon carbide powder, molybdenum disilicide, tungsten disilicide, and zirconium diboride, and from about 1% to about 5% of a stabilizer taken from the group consisting of bentonite, kaolin, magnesium alumina silica clay, tabular alumina, and stabilized zirconium oxide;
  c. from about 10% to about 30% colloidal silica, from about 50% to about 79% silicon dioxide powder, and from about 2% to about 15% of one or more emissivity agents taken from the group consisting of iron oxide, boron silicide, boron carbide, silicon tetraboride, silicon carbide molybdenum disilicide, tungsten disilicide, and zirconium diboride; or d. from about 10% to about 30% colloidal silica, from about 50% to about 79% silicon dioxide powder, from about 2% to about 15% of one or more emissivity agents taken from the group consisting of iron oxide, boron silicide, boron carbide, silicon tetraboride, silicon carbide molybdenum disilicide, tungsten disilicide, and zirconium diboride, and from about 1.5% to about 5.0% of a stabilizer taken from the group consisting of bentonite, kaolin, magnesium alumina silica clay, tabular alumina, and stabilized zirconium oxide.

15. The process of claim 11, wherein:

a second thermal process tube is provided about the first thermal process tube encompassing the first thermal process tube therein the thermal process tube having first and second ends, wherein the second end is closed;

such that a fluid entering through the first end of the first thermal tube is ejected out of an opening dispose adjacent the first end of the second thermal tube.

16. The process of claim 15, wherein:

a thermal protective layer contains a. from about 10% to about 30% sodium silicate, from about 50% to about 79% silicon dioxide powder, and from about 4% to about 15% of one or more emissivity agents taken from the group consisting of iron oxide, boron silicide, boron carbide, silicon tetraboride, silicon carbide powder, molybdenum disilicide, tungsten disilicide, and zirconium diboride;

b. from about 10% to about 30% sodium silicate, from about 50% to about 79% silicon dioxide powder, from about 4% to about 15% of one or more emissivity agents taken from the group consisting of iron oxide, boron silicide, boron carbide, silicon tetraboride, silicon carbide powder, molybdenum disilicide, tungsten disilicide, and zirconium diboride, and from about 1% to about 5% of a stabilizer taken from the group consisting of bentonite, kaolin, magnesium alumina silica clay, tabular alumina, and stabilized zirconium oxide;

c. from about 10% to about 30% colloidal silica, from about 50% to about 79% silicon dioxide powder, and from about 2% to about 15% of one or more emissivity agents taken from the group consisting of iron oxide, boron silicide, boron carbide, silicon tetraboride, silicon carbide molybdenum disilicide, tungsten disilicide, and zirconium diboride; or d. from about 10% to about 30% colloidal silica, from about 50% to about 79% silicon dioxide powder, from about 2% to about 15% of one or more emissivity agents taken from the group consisting of iron oxide, boron silicide, boron carbide, silicon tetraboride, silicon carbide molybdenum disilicide, tungsten disilicide, and zirconium diboride, and from about 1.5% to about 5.0% of a stabilizer taken from the group consisting of bentonite, kaolin, magnesium alumina silica clay, tabular alumina, and stabilized zirconium oxide.

17. The process of claim 12, wherein:

a second thermal process tube is provided about the first thermal process tube encompassing the first thermal process tube therein the thermal process tube having first and second ends, wherein the second end is closed;

such that a fluid entering through the first end of the first thermal tube is ejected out of an opening dispose adjacent the first end of the second thermal tube.

* * * * *